US008357353B2

(12) United States Patent
Laszlo et al.

(10) Patent No.: US 8,357,353 B2
(45) Date of Patent: Jan. 22, 2013

(54) COMPOSITIONS COMPRISING A UV-ABSORBING CHROMOPHORE

(75) Inventors: Joseph A. Laszlo, Peoria, IL (US); David L. Compton, Peoria, IL (US); Louis J. DeFilippi, Palatine, IL (US); Steven Grall, Lemont, IL (US)

(73) Assignees: Biotechnology Research & Development Corporation, Peoria, IL (US); United States Department of Agriculture, Peoria, IL (US)

( * ) Notice: Subject to any disclaimer, the term of this patent is extended or adjusted under 35 U.S.C. 154(b) by 233 days.

(21) Appl. No.: 12/776,876

(22) Filed: May 10, 2010

(65) Prior Publication Data
US 2010/0215600 A1 Aug. 26, 2010

Related U.S. Application Data

(62) Division of application No. 11/425,094, filed on Jun. 19, 2006, now Pat. No. 7,727,514.

(60) Provisional application No. 60/723,209, filed on Oct. 3, 2005.

(51) Int. Cl.
A61K 8/00 (2006.01)
A61K 8/18 (2006.01)
A61Q 17/04 (2006.01)

(52) U.S. Cl. .......................................... 424/59
(58) Field of Classification Search ............ 424/59
See application file for complete search history.

(56) References Cited

U.S. PATENT DOCUMENTS

| | | | |
|---|---|---|---|
| 3,153,659 | A | 10/1964 | King |
| 5,155,244 | A | 10/1992 | Greene et al. |
| 5,380,890 | A | 1/1995 | Greene et al. |
| 5,614,648 | A | 3/1997 | Greene et al. |
| 5,683,683 | A | 11/1997 | Scafidi |
| 5,817,299 | A | 10/1998 | Manirazman |
| 5,902,591 | A | 5/1999 | Herstein |
| 6,013,270 | A | 1/2000 | Hargraves et al. |
| 6,346,236 | B1 | 2/2002 | Compton et al. |
| 6,372,234 | B1 | 4/2002 | Deckers et al. |
| 6,565,865 | B2 | 5/2003 | Bekele |
| 6,890,520 | B2 | 5/2005 | Taniguchi et al. |
| 7,163,673 | B2 | 1/2007 | Compton et al. |
| 7,223,770 | B2 | 5/2007 | Zhang et al. |
| 7,351,403 | B2 | 4/2008 | Harry-O'kuru |
| 7,572,610 | B2 | 8/2009 | Laszlo et al. |
| 7,727,514 | B2 | 6/2010 | Laszlo et al. |
| 7,744,856 | B2 | 6/2010 | DeFilippi et al. |
| 2001/0021375 | A1 | 9/2001 | Hossel et al. |

FOREIGN PATENT DOCUMENTS

| | | |
|---|---|---|
| WO | 9533706 A1 | 12/1995 |
| WO | 0172683 A1 | 10/2001 |
| WO | 2007041424 A1 | 4/2007 |
| WO | 2008003090 A2 | 1/2008 |
| WO | 2008003090 A3 | 1/2008 |

OTHER PUBLICATIONS

Foreign communication from a related counterpart application—Examination Report dated Nov. 26, 2010 (2 pages), Australian Application No. 2006299576 filed on May 2, 2008.
Foreign communication from a related counterpart application—Examination Report dated Dec. 10, 2008 (4 pages), European Application No. 06 815 941.7 filed on May 2, 2008.
Foreign communication from a related counterpart application—Office Action (with translation) dated Dec. 1, 2009 (11 pages), Mexican Application No. MX/a/2008/005781 filed on May 2, 2008.
Foreign communication from a related counterpart application—Examination Report dated Jan. 22, 2010 (2 pages), New Zealand Application No. 567881 filed on May 2, 2008.
Foreign communication from a related counterpart application—Office Action (with translation) dated Jul. 27, 2010 (9 pages), Mexican Application No. MX/a/2008/005781 filed on May 2, 2008.
Foreign communication from a related counterpart application—Examination Report, European Application No. 06815941.7, Mar. 1, 2011, 11 pages.
Batovska, Daniela I., et al., "Synthesis of some phenylpropanoid monoglycerides via the Mitsunobu protocol." Molecules, 2005, pp. 552-558, vol. 10, MDPI.
Compton, David L., et al., "Lipase-catalyzed synthesis of ferulate esters," JAOCS, 2000, pp. 513-519, vol. 77, No. 5, AOCS Press.
Cooper, Raymond, et al., "New phenolic diglycerides from *Aegilops ovata*," Phytochemistry, 1978, pp. 1673-1675, vol. 17, Pergamon Press Ltd.
Foreign communication from a related counterpart application—International Search Report and Written Opinion, PCT/US2006/038300, Feb. 7, 2007, 17 pages.
Foreign communication from a related counterpart application—International Preliminary Report on Patentability, PCT/US2006/038300, Apr. 17, 2008, 13 pages.

(Continued)

*Primary Examiner* — Mina Haghighatian
*Assistant Examiner* — Luke Karpinski
(74) *Attorney, Agent, or Firm* — Conley Rose, P.C.; Rodney B. Carroll (57) ABSTRACT

A chemical composition comprising a linker agent and a compound comprising at least one UV-absorbing chromophore, wherein the linker agent is characterized by the general formula:

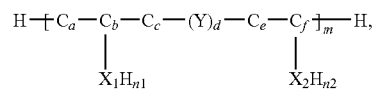

wherein $X_1$ and $X_2$ are the same or different, and at least one of $X_1$ or $X_2$ is a functional group that bonds with the compound comprising at least one UV-absorbing chromophore, and $b+f \geq 2$, Y comprises an O, N, or S that is substituted or unsubstituted, each a, b, c, e and f is $\geq 0$ and $a+b+c+e+f \geq 2$, d is 0 or 1, n1 and n2 represent the number of hydrogen atoms required to complete the undesignated valencies, and m ranges from 1 to about 100 and each individual m unit may be the same or different.

21 Claims, 6 Drawing Sheets

OTHER PUBLICATIONS

Foreign communication from a related counterpart application—International Search Report, PCT/US07/72557, Feb. 27, 2008, 3 pages.

Foreign communication from a related counterpart application—International Preliminary Examination Report, PCT/US07/72557, Oct. 7, 2009, 12 pages.

Guyot, B., et al., "Esterification of phenolic acids from green coffee with an immobilized lipase from *Candida antarctica* in solvent-free medium," Biotechnology Letters, Jun. 1997, pp. 529-532, vol. 19, No. 6, Chapman & Hall.

Hatfield, Ronald D., et al., "Synthesis of methyl 5-O-trans-Feruloyl-a-L-arabinofuranoside and its use as a substrate to assess feruloyl esterase activity," Analytical Biochemistry, 1991, pp. 25-33, vol. 194, Academic Press, Inc.

Helm, Richard F., et al., "Synthesis of feruloylated and p-coumaroylated methyl glycosides," Carbohydrate Research, 1992, pp. 183-194, vol. 229, Elsevier Science Publishers, B.V., Amsterdam.

Holser, R. A., et al., "Preparation and characterization of 4-methoxy cinnamoyl glycerol," J Am Oil Chem Soc, 2008, pp. 347-351, vol. 85, AOCS.

Holser, Ronald A., "Kinetics of cinnamoyl glycerol formation," J Am Oil Chem Soc, 2008, pp. 221-225, vol. 85, AOCS.

Jang, Dae Sik, et al., "Constituents of *Asparagus officinalis* evaluated for inhibitory activity against cyclooxygenase-2," Journal of Agricultural Food Chemistry, 2004, pp. 2218-2222, vol. 52, No. 8, American Chemical Society.

Laszlo, Joseph A., et al., "Enzymatic glycerolysis and transesterification of vegetable oil for enhanced production of feruloylated glycerols," XP002415387, Jan. 16, 2007, 1 page, Biosis.

Laszlo, Joseph A., et al., "Packed-bed bioreactor synthesis of feruloylated monoacyl- and diacylglycerols: clean production of a "green" sunscreen," Green Chemistry, 2003, pp. 382-386, vol. 5, The Royal Society of Chemistry.

Lin, Fu-Hsiung, et al., "Ferulic acid stabilizes a solution of vitamins C and E and doubles its photoprotection of skin," The Journal of Investigative Dermatology, Oct. 4, 2005, pp. 826-832, vol. 125, The Society for Investigative Dermatology, Inc.

Lu, Fachuang, et al., "Facile synthesis of 4-hydroxycinnamyl p-coumarates," J. Agric. Food Chem., 1998, pp. 2911-2913, vol. 46, No. 8, American Chemical Society.

Mimaki, Yoshihiro, et al., "Steroidal saponins from the bulbs of *Lilium brownii*," Phytochemistry, 1990, pp. 2267-2271, vol. 29, No. 7, Pergamon Press plc.

Provisional patent application entitled "Accelerated feruloylation of vegetable oils," by Joseph A Laszlo, et al., filed Oct. 3, 2005 as U.S. Appl. No. 60/723,209.

Sabally, Kebba, et al., "Lipase-catalyzed transesterification of dihydrocaffeic acid with flaxseed oil for the synthesis of phenolic lipids," Journal of Biotechnology, 2006, pp. 167-176, vol. 127, Elsevier B.V.

Safari, Mohammad, et al., "Enzymatic synthesis of structured phenolic lipids by incorporation of selected phenolic acids into triolein," XP002415385, Jan. 16, 2007, 1 page, Biosis.

Sun, Shangde, et al., "A novel, two consecutive enzyme synthesis of feruloylated monoacyl- and diacyl-glycerols in a solvent-free system," Biotechnol Lett, 2007, pp. 1947-1950, vol. 29, Springer Science+Business Media B.V.

Sun, Shangde, et al., "Solvent-free enzymatic synthesis of feruloylated diacylglycerols and kinetic study," Journal of Molecular Catalysis B: Enzymatic, 2007, pp. 1-20 plus 1 publication disclosure page.

Sun, Shangde, et al., "Solvent-free synthesis of glyceryl ferulate using a commercial microbial lipase," Biotechnol Lett, 2007, pp. 945-949, vol. 29, Springer Science+Business Media B.V.

Torres, Carlos F., et al., "Lipase-catalyzed synthesis of designer acyl-glycerols rich in residues of eicosapentaenoic, docosahexaenoic, conjugated linoleic, and/or stearic acids," Eur. J. Lipid Sci. Technol., 2003, pp. 614-623, vol. 105, Wiley-VCH Verlag GmhH & Co. KGaA, Weinheim.

Tsuchiyama, Moriyasu, et al., "Esterification of ferulic acid with polyols using a ferulic acid esterase from *Aspergillus niger*," Biochimica et Biophysica Acta, 2006, pp. 1071-1079, vol. 1760, Elsevier B.V.

Tsuchiyama, Moriyasu, et al., "Esterification of ferulic acid with polyols using a ferulic acid esterase from *Aspergillus niger*," XP002415386, Jan. 16, 2007, 1 page, Biosis.

Warner, K., et al., "Addition of ferulic acid, ethyl ferulate, and feruloylated monoacyl- and diacylglycerols to salad oils and frying oils," JAOCS, 2005, pp. 647-652, vol. 82, No. 9, AOCS Press.

Xin, Jia-Ying, et al., "Lipase-catalyzed synthesis of ferulyl oleins in solvent-free medium," Food Chemistry, 2009, pp. 640-645, vol. 112, Elsevier Ltd.

COMPOSITIONS COMPRISING A UV-ABSORBING CHROMOPHORE

CROSS-REFERENCE TO RELATED APPLICATIONS

This is a Divisional Application of U.S. patent application Ser. No. 11/425,094, filed on Jun. 19, 2006, published as U.S. Patent Publication No. US 2007/0077214A1, and entitled "Compositions Comprising a UV-Absorbing Chromophore," which claims priority to U.S. Provisional Application Ser. No. 60/723,209, filed Oct. 3, 2005 and entitled "Accelerated Feruloylation of Vegetable Oils," each of which is incorporated herein by reference. This application is related to commonly owned U.S. patent application Ser. No. 11/425,096 filed Jun. 19, 2006, now U.S. Pat. No. 7,572,610, and entitled "Methods of Making Compositions Comprising a UV-Absorbing Chromophore," which is hereby incorporated by reference herein in its entirety.

STATEMENT REGARDING FEDERALLY SPONSORED RESEARCH OR DEVELOPMENT

Not applicable.

FIELD OF THE INVENTION

The present disclosure relates generally to compositions comprising UV-absorbing chromophores such as phytochemicals and methods of production of same. More specifically, the present disclosure relates to fat soluble compositions comprising feruloylated vegetable oils and methods for the acylation of polyols.

BACKGROUND OF THE INVENTION

Phytochemicals are broadly known to be any chemical or nutrient derived from a plant source. The term phytochemicals may also refer to compounds found in plants that are not required for normal functioning of the human body but that may have a positive impact on body function. For example, phytochemicals may promote immune system function, possess antibiotic, antiviral, antineoplastic or antiinflammatory activity; and be associated with the treatment or prevention of maladies such as cancer or cardiovascular disease. Given the wealth of possible beneficial effects of phytochemicals, these compounds may be incorporated into a variety of consumer products such as for example nutritional supplements such as vitamins and topical protectants such as sunscreen.

It is well established that UV radiation with wavelengths between 290 nm and 400 nm damages the human epidermis. Even brief exposure to UVB radiation (wavelengths between about 290 nm and about 320 nm) can cause sunburn, while long-term exposure to UVA radiation (wavelengths between about 320 nm and about 400 nm) can cause skin cancer (melanoma) and premature aging of the skin (including wrinkling, loss of elasticity, and pigment changes). Thus, there is a significant demand for inexpensive, effective sunblocks and sunscreens.

The most commonly used sunscreens are UV filters, which typically organic compounds are incorporated at levels of about 2-15% into topical formulations. A disadvantage of UV filters is that each organic compound has a limited range of effective UV absorptivity, rendering each compound better suited for either UVA protection or UVB protection but not both. The advantage of the UV filtering molecules, however, is that they can be engineered to provide sunscreens with desirable physical appearance, solubility, and water resistant properties.

One such approach to the formation of effective sunscreens entails the formation of structured lipids with specific UV-absorbing properties. It is known that covalent substitution of ferulic acid onto the glycerol backbone of triacylglycerols generates commercially-useful ultraviolet light absorbing lipids. As disclosed in U.S. Pat. No. 6,346,236, which is incorporated herein by reference, one technique for feruloylation of vegetable oils entails a prolonged lipase treatment of ethyl ferulate and triacylglycerol. However, this reaction, a transesterification, is slow and takes on the order of days to reach equilibrium at 60° C.

Thus, there is an ongoing need for improved phytochemical-containing compositions and methods of making same. Additionally, in order to improve the commercial value of sunscreens and other phytochemical-containing products produced from vegetable oils, it remains desirable to enhance the rate and yield of the transesterification reaction.

SUMMARY OF THE INVENTION

Disclosed herein is a chemical composition comprising a linker agent and a compound comprising at least one UV-absorbing chromophore, wherein the linker agent is characterized by the general formula:

wherein $X_1$ and $X_2$ are the same or different, and at least one of $X_1$ or $X_2$ is a functional group that bonds with the compound comprising at least one UV-absorbing chromophore, and $b+f \geq 2$, Y comprises an O, N, or S that is substituted or unsubstituted, each a, b, c, e and f is $\geq 0$ and $a+b+c+e+f \geq 2$, d is 0 or 1, n1 and n2 represent the number of hydrogen atoms required to complete the undesignated valencies, and m ranges from 1 to about 100 and each individual m unit may be the same or different.

Also disclosed herein is a fat soluble composition comprising a mono or diacylglycerol esterified with a plant-derived functional group comprising an aromatic species, an unsaturated isoprenoid, an unsaturated terpenoid, a hindered hydroxy-substituted cinnamic acid, an unhindered hydroxy-substituted cinnamic acid or combinations thereof.

Also disclosed herein is a fat-soluble composition, comprising a glycerol esterified with a plant-derived functional group comprising maleanilic acid, homovanillic acid, folic acid, crocetin, coumaric acid, caffeic acid, ferulic acid, sinapic acid (sinapinic acid), derivatives thereof or combinations thereof, wherein the esterified glycerol includes at least two plant-derived functional groups.

Also disclosed herein is a chemical composition comprising a linker agent and a compound comprising at least one UV absorbing chromophore, wherein the linker agent is characterized by the general formula:

wherein $X_1$ and $X_2$ are the same or different at least one of $X_1$ or $X_2$ is a functional group that bonds with the compound comprising at least one UV-absorbing chromophore, and $b+f \geq 2$, $X_3$ and $X_4$ are the same or different and $X_3$, $X_4$ or both is a hydrophobic moiety, Y comprises an O, N, or S that is substituted or unsubstituted, each a, b, c, e and f is $\geq 0$ and $a+b+c+e+f \geq 2$, d is 0 or 1, n1 and n2 represent the number of hydrogen atoms required to complete the undesignated valencies, and m ranges from 1 to about 100 and each individual m unit may be the same or different.

Also disclosed herein is a chemical composition comprising at least two compounds having the general formula:

wherein $X_1$ and $X_2$ are different at least one of $X_1$ or $X_2$ is a functional group that bonds with a compound comprising at least one UV-absorbing chromophore, and $b+f \geq 2$, $X_3$ and $X_4$ are the same or different and $X_3$, $X_4$ or both is a hydrophobic moiety, Y comprises an O, N, or S that is substituted or unsubstituted, each a, b, c, e and f is $\geq 0$ and $a+b+c+e+f \geq 2$, d is 0 or 1, n1 and n2 represent the number of hydrogen atoms required to complete the undesignated valencies, m ranges from 1 to about 100 and each individual m unit may be the same or different, and wherein the compound comprising at least one UV-absorbing chromophore comprises a phytochemical which further comprises an aromatic species, an unsaturated isoprenoid, an unsaturated terpenoid, a hindered hydroxy-substituted cinnamic acid, an unhindered hydroxy-substituted cinnamic acid or combinations thereof.

The foregoing has outlined rather broadly the features and technical advantages of the present invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more detailed description of the present invention, reference will now be made to the accompanying drawings, wherein.

DETAILED DESCRIPTION OF THE PREFERRED EMBODIMENT

Disclosed herein are chemical compositions comprising a linker agent and at least one compound comprising at least one UV-absorbing chromophore and methods of making same. In an embodiment, the compound comprising at least one UV-absorbing chromophore comprises a phytochemical. The chemical compositions may further comprise a carrier agent. The phytochemicals suitable for use in this disclosure may exhibit a variety of desirable properties such as the ability to absorb ultraviolet radiation and/or antineoplastic activity. The chemical compositions disclosed may be incorporated into formulations for use in topical products, pharmaceutical products, nutritional products and other applications as will be described in more detail herein. Hereafter the discussion will focus on the use of phytochemicals as the compounds comprising at least one UV-absorbing chromophore in the disclosed compositions however other compounds comprising at least one UV-absorbing chromophore may also be employed in the compositions. Such other compounds containing at least one UV-absorbing chromophore may be known to one of ordinary skill in the art. Hereafter the chemical compositions comprising a linker agent, at least one phytochemical and an optional carrier agent will be referred to as phytochemical-containing compositions (PCCs).

Throughout the following disclosure certain acronyms are used for expediency. They are as follows: EF: ethyl ferulate; FG: feruloyl glycerol (one feruloyl moiety and no fatty acid moieties per glycerol moiety); $F_2G$: diferuloyl glycerol (two feruloyl moieties and no fatty acid moieties per glycerol moiety); FMOG: feruloyl monooleoyl glycerol; $F_2MOG$: diferuloyl monooleoyl glycerol; FDOG: feruloyl dioleoyl glycerol; FMAG: feruloyl monoacylglycerol (one feruloyl moiety and one fatty acid moiety per glycerol); $F_2MAG$: diferuloyl monoacylglycerol (two feruloyl moieties and one fatty acid moiety per glycerol moiety); and FDAG: feruloyl diacylglycerol (one feruloyl moiety and two fatty acid moieties per glycerol moiety).

In an embodiment, the PCC comprises a linker agent. The linker agent may be any compound that can react to covalently bond with a phytochemical and an optional carrier agent. Alternatively, the linker agent may be a compound characterized by the general formula:

wherein $X_1$ and $X_2$ are the same or different, and at least one of $X_1$ or $X_2$ is a functional group that is capable of bonding with the phytochemical, and $b+f \geq 2$. Y may comprise an O, N, or S that is substituted or unsubstituted; each a, b, c, e and f is $\geq 0$ and $a+b+c+e+f \geq 2$; d is 0 or 1; n1 and n2 represent the number of hydrogen atoms required to complete the undesignated valencies; and m ranges from about 1 to about 100. In some embodiments wherein m is greater than 1, the individual m units comprising the linker agent may be the same or different. In an embodiment, the linker agent further comprises a terminal carbon atom, $C_g$, that is adjacent $C_f$, wherein $g \geq 1$. In some embodiments, the substituents on the C groups, the Y groups, or combinations thereof may form cyclic structures. Examples of such cyclic structures include without limitation 1,2-cyclohexanediol, 1,3-cyclopentanediol, cyclopentene-1,3-diol. In such embodiments, the cyclic structures formed may not comprise acetals or hemiacetals.

In an embodiment, the linker agent comprises a polyvinyl alcohol, an amine, a diol, a triol, a thiol or combinations thereof. Examples of such compounds include without limitation ethylene glycol, ethylenediamine, 1,2-propylene glycol, 1,3-propylene glycol, glycerol, 2-mercaptoethanol, 2-ethanolamine, 1,4-butanediol, diethylene glycol, or combinations thereof. Such linker agents may be produced by any means known to one of ordinary skill in the art. Alternatively, the linker agent is produced by chemical modification of a triacylglycerol as will be described in more detail later herein.

In an embodiment, the PCC comprises a compound containing at least one UV-absorbing chromophore. Alternatively the PCC comprises a phytochemical. As used herein, "phytochemicals" are non-nutritive plant chemicals that have protective or disease preventive properties. Phytochemicals suitable for use in this disclosure may possess desirable characteristics such as for example UV absorbing properties, anti-aging properties, anti-bacterial, anti-neoplastic properties, anti-oxidant properties, anti-viral or other photoactive, bioactive, or optical properties. In some embodiments, acyl esters of various phytochemicals are among the compounds that may be used in the present techniques. Substitution of various phytochemicals onto the linker agent may produce compositions with lesser water-soluble properties and greater oil soluble properties (often described as an increase in the oil-water partition coefficient) having desirable properties corresponding to those of the component phytochemicals. Examples of suitable phytochemicals include but are not limited to: flavonoids, isoflavones (phytoestrogens), isothiocyanates, organosulfur compounds, saponins, capsaicin, sterols, and particularly hydroxycinnamic acid derivatives such as coumaric, caffeic, chlorogenic, ferulic and sinapic acids.

In an embodiment, the phytochemical comprises any carboxyl containing phytochemical. Alternatively, the phytochemical comprises an aromatic species, an unsaturated isoprenoid, an unsaturated terpenoid, a hindered hydroxy-substituted cinnamic acid, an unhindered hydroxy-substituted cinnamic acid or combinations thereof. In embodiments wherein the phytochemical comprises a hydroxy substituted cinnamic acid, the substituents may be located at positions 2, 3, 4, 5, 6 or combinations thereof. Examples of phytochemicals suitable for use in this disclosure include without limitation maleanilic acid, homovanillic acid, folic acid, crocetin, coumaric acid, caffeic acid, ferulic acid, sinapic acid, derivatives thereof or combinations thereof. Useful properties attributed to those chemicals include antioxidant properties, simulation of hormonal action, stimulation of enzymes, interference with DNA replication, and anti-bacterial activity.

As will be understood by one of ordinary skill in the art the incorporation of a phytochemical in the PCC may result in slight modifications of the phytochemical however, the compositions and methodologies disclosed herein allow the phytochemical in the PCC to retain the beneficial properties associated with the phytochemical. The final compositions disclosed herein are designated as PCC however, such compositions may comprise a slightly modified phytochemical or phytochemical derivative such as for example and without limitation a phytochemical having been deprotonated to allow for the formation of a covalent bond with another component described herein such as for example a linker agent.

In an embodiment, the PCC comprises an optional carrier agent. The carrier agent may function to increase the lipid solubility of the composition thus the carrier agent may be any hydrophobic compound that renders the entire PCC water insoluble. Examples of suitable carrier agents include without limitation hydrogen, fatty acids, monoterpenes, diterpenes, triterpenes, or combinations thereof. In an embodiment, the carrier agent comprises a fatty acid for example a $C_2$-$C_{24}$ fatty acid moiety having varying degrees of saturation from completely saturated to tri-unsaturated. Alternatively, the carrier agent may comprise a non-fatty acid carboxylate.

In an embodiment, the PCC comprises a linker agent and at least two phytochemicals. In such embodiments, the linker agent may be a compound characterized by the general formula:

wherein $X_1$ and $X_2$ are the same or different, and at least two of $X_1$ or $X_2$ is a functional group that is capable of bonding with the phytochemical, and $b+f \geq 2$, Y may comprise an O, N, or S that is substituted or unsubstituted; each a, b, c, e and f is $\geq 0$ and $a+b+c+e+f \geq 2$, d is 0 or 1; n1 and n2 represent the number of hydrogen atoms required to complete the undesignated valencies; and m ranges from 1 to about 100. In some embodiments wherein m is greater than 1, the individual m units comprising the linker agent may the same or different. In an embodiment, $b \geq 3$ and the PCC comprises at least two phytochemicals of the type disclosed herein. The phytochemicals may be the same or different. In such embodiments, $X_1$, $X_2$ or both are bonded with the phytochemicals.

In an embodiment, the PCC comprises a compound having the general formula:

wherein at least two of $R_1$, $R_2$, and $R_3$ are non-fatty acid carboxylates; and the other of $R_1$, $R_2$, and $R_3$ are each either a $C_2$-$C_{24}$ fatty acid moiety, OH, or a non-fatty acid carboxylate, wherein the first and second non-fatty acid carboxylates are the same or different. In such embodiments, the first non-fatty acid carboxylate may comprise a first phytochemical and the second non-fatty acid carboxylate may comprise a second phytochemical, wherein the first and second phytochemicals are the same or different and may be of the type previously disclosed herein.

In an embodiment, the PCC comprises a compound characterized by the general formula II:

II wherein $R_4$=H or $OCH_3$ and $R_2,R_3$ or both are non-fatty acid carboxylates comprising phytochemicals of the type disclosed herein. For simplicity, the double bond in the compound characterized by general formula II is depicted in the trans isomeric form. As would be understood by one of ordinary skill in the art, the cis isomeric form may also be present in varying percentages.

In some embodiments, the PCC may comprise a linker agent and at least one phytochemical wherein the linker agent is characterized by the general formula:

wherein $X_1$ and $X_2$ are the same or different at least one of $X_1$ or $X_2$ is a functional group that is capable of bonding with the phytochemical, and $b+f \geqq 2$; $X_3$ and $X_4$ are the same or different and $X_3$, $X_4$ or both is a hydrophobic moiety; Y may comprise an O, N, or S that is substituted or unsubstituted; each a, b, c, e and f is $\geqq 0$ and $a+b+c+e+f \geqq 2$, d is 0 or 1; n1 and n2 represent the number of hydrogen atoms required to complete the undesignated valencies; and m ranges from 1 to about 100. In some embodiments wherein m is greater than 1, the individual m units comprising the linker agent may the same or different.

In such embodiments, $X_3$, $X_4$ or both may function to increase the lipid solubility of the composition in the presence or absence of a carrier agent. For example and without limitation, $X_3$, $X_4$ or both may comprise a derivatizable naturally occurring lipid. In an embodiment, $X_3$ may comprise a moiety characterized by the general formula:

—CH=CH—$(CH_2)_n$$CH_3$, where n may range from about 8 to about 24, alternatively n may range from about 12 to about 24, alternatively n is 12. In an embodiment, $X_4$ may comprise a moiety characterized by the general formula:

—NCO—$(CH_2)$—CH=CH—$(CH_2)_7$$CH_3$.

Alternatively, $X_3$, $X_4$ or both comprises sphingosine, ceramide or combinations thereof.

In an embodiment, the PCC comprises caffeic acid. In such embodiments, the PCC may not comprise glycerol as a linker agent.

In an embodiment, the PCC may be produced using any means known to one of ordinary skill in the art. Alternatively, the PCC may be produced by transesterification of a mono- or diacylglycerol according to the methods disclosed herein.

It has been discovered that, unexpectedly, the rate of transesterification with a desired non-fatty acid carboxylate can be increased two- to seven-fold by prior or concomitant partial deacylation of a triacylglycerol. By partially deacylating the triacylglycerol or providing mono- or diacylglycerol as a reagent, the rate of transesterification with the desired carboxylate is increased.

In an embodiment, the glycerol is a triacylglycerol, for example and without limitation a natural vegetable oil. In an embodiment, the vegetable oil comprises soybean oil, corn oil, sunflower seed oil, high-oleic sunflower seed oil, canola oil, safflower oil, *cuphea* oil, coconut oil, palm kernel oil, olive oil or combinations thereof. These oils may have fatty acid moieties ranging in length from $C_2$-$C_{24}$, and having varying degrees of saturation from completely saturated to hexa-unsaturated. Hydroxyl-substituted oils, such as ricinoleic, are also contemplated. When the products of the invention are intended for use in cosmetic formulations, it is preferred to select vegetable oils that are aromatically pleasing, particularly those having a relatively low level of linolenic acid, for example. Synthetic triglycerides, such as triolein, can also be used as the starting material.

The transesterification reactions described herein may be carried out in the presence of a biocatalyst. In an embodiment, the biocatalyst is a hydrolase, alternatively an esterase, alternatively a lipase. A lipase suitable for use herein is one having regioselective specificity towards the terminal acyl groups of a triacylglycerol. While there are several suitable enzymes, as will be recognized by those skilled in the art, one such lipase is produced by *Candida antarctica*. This enzyme on an inert support is produced by Novo Nordisk (Franklinton, N.C., USA) under the tradename Novozym® 435.

As mentioned previously, it has been discovered that removal of one or more of the fatty acids from the linker agent backbone (e.g., glycerol) prior to transesterification with the desired functional moiety significantly enhances the subsequent rate of transesterification. In addition, deacylation of the triacylglycerol prior to transesterification may increase the production of diaryl-substituted glycerols. As will be understood by one of ordinary skill in the art, the starting reagent may alternatively comprise a polyol (e.g., glycerol) that has been reacted with a fatty acid in an esterification reaction to produce a mono or diacylglycerol.

Mono- and/or diacylglycerols suitable for use in the present techniques may be produced from triacylglycerols by one of several processes, including but not limited to:
 (1) partial alcoholysis of triacylglycerols, followed by distillation to remove the produced fatty esters,
 (2) partial hydrolysis of triacylglycerols followed by distillation to remove the produced fatty acids,
 (3) partial transesterification of glycerol with free fatty acids (such as the 1,3-diacylglycerol sold under the trade name Enova™ oil), or
 (4) transesterification with glycerol or any of the linker agents disclosed herein.

Alcoholysis may be conducted using short-chain alcohols such as ethanol or propanol, or by glycerol (glycerolysis), which is particularly efficacious in this instance because no subsequent distillation step is required. By way of example only, soybean oil (SBO) can be emulsified with ethanol at a 1:4 w/w ratio and then treated with Novozym 435 (10:1 w/w substrate to enzyme ratio) at room temperature for 4 hours. The enzyme can be separated from the product by filtration and excess ethanol removed by rotary evaporation. The resulting preparation of sn-2-monoacylglycerols (2-MAG) can be separated from ethyl fatty acid esters by molecular distillation.

The mono- and/or diacylglycerols can in turn be esterified with a compound having desired properties. For example, the mono and/or diacylglycerols may be esterified with the phytochemicals disclosed herein. In an embodiment, the phytochemical comprises ethyl ferulate and the linker agent comprises glycerol. In such embodiments, transesterification of the glycerol under the conditions disclosed herein may produce diferuloyl-MAG ($F_2MAG$) and diferuloyl glycerol ($F_2G$), as described in detail below. While certain embodiments of the present disclosure are described herein with respect to feruloyl or coumaroyl compounds, it will be understood that the present disclosure is advantageous in the manufacture of glycerols substituted with various other compounds as well.

The transesterification (glycerolysis) reaction is optimally conducted in the absence of oxygen, such as in vacuo or under an inert gas such as nitrogen. The reaction may be carried out in a solventless system, or alternatively, using toluene or other suitable solvent for both the glyceride and the ferulate or coumarate ester reactants and also for the lipase catalyst. In an embodiment, the transesterification reaction may be carried out in the substantial absence of water. Alternatively, the transesterification reaction may be carried out in a solvent having a water activity of from about 0 to about 0.6, alternatively less than about 0.25. Temperature conditions for the reaction may range from about 20° C. to about 65° C., with the preferred temperatures being in the range of about 55° C. to about 60° C.

As discussed in detail below, the lipase-catalyzed synthesis of PCCs comprising glycerol as a linker agent and ferulic acid as a phytochemical results in the exchange of one fatty acid group for one ferulic acid group. As both reactants are esters on separate molecules, this exchange is formally a transesterification. However, within the reactive site of the lipase, the reaction proceeds stepwise, with the transient formation of an esterified enzyme. Thus, it is generally believed by those knowledgeable in the field that prior treatment of the triacylglycerol with an alcohol to liberate a reactive hydroxyl position on the glycerol backbone is unnecessary. Despite this expectation, however, we have discovered that the rate of transesterification of oils with ethyl ferulate substantially increases when the oil is, wholly or in part, a mono- and/or diacylglycerol.

In the case of feruloylated glycerols, this rate enhancement improves the efficiency and production throughput of Soy-Screen™ manufacture, and proportionally lowers its cost of production. The final product is a compound having a linker agent of the type disclosed herein, at least one of the desired carboxylate groups bonded thereto, and optionally at least one other group also bonded to the backbone, wherein the other group is either a $C_2$-$C_{24}$ fatty acid moiety, OH, or a non-fatty acid carboxylate.

In addition to the discovery that partially deacylated glycerides are more rapidly esterified, it has further been discovered that monoacylated glycerides react more rapidly than diacylated glycerides. By way of example only, feruloylation of 2-MAG achieved a 46±1% product yield in 24 hours, compared to 38% for Enova diacylglycerol oil (EDO).

The transesterification reactions described may be used to produce a PCC of the type disclosed herein. In some embodiments, prior to or following recovery of the PCC from the reaction mixture, the PCC may be subjected to additional reactions intended to remove or reduce the amount of volatile compounds in the PCC. Any reaction useful for the reduction or removal of volatile compounds from the PCC and compatible with the components of the PCC as known to one of ordinary skill in the art may be employed. In an embodiment, prior to or following recovery of the PCC from the reaction mixture, the PCC may be subjected to additional reactions intended to remove at least a portion of any unreacted triacylglycerol from the PCC. Any reaction useful for the removal of unreacted triacylglycerol from the PCC and compatible with the components of the PCC as known to one of ordinary skill in the art may be employed.

The PCCs and methods of production disclosed herein may be used in the manufacture of numerous products ranging from cosmetics to nutritional supplements. In an embodiment, a formulation for use in the manufacture of a consumer product may comprise at least one PCC produced by the methodologies of the present disclosure. In such embodiments, the PCC may absorb primarily UVA radiation, primarily UVB radiation, or both. In one embodiment, a formulation for use in the manufacture of a consumer product may comprise at least one PCC of the type disclosed herein wherein the PCC absorbs both UVA and UVB radiation. In alternative embodiments, the PCC may possess anti-aging properties, anti-neoplastic properties, antibacterial, properties, antioxidant properties or combinations thereof. In an embodiment the consumer product may comprise a lotion, a sunscreen, a food supplement, a nutritional product, an agrochemical, a pharmaceutical product or combinations thereof.

EXAMPLES

The invention having been generally described, the following examples are given as particular embodiments of the invention and to demonstrate the practice and advantages thereof. It is understood that the examples are given by way of illustration and are not intended to limit the specification of the claims to follow in any manner. Throughout the following examples certain acronyms are used for expediency. They are as follows: EF: ethyl ferulate; FG: feruloyl glycerol; $F_2G$: diferuloyl glycerol; FMOG: feruloyl monooleoyl glycerol; $F_2MOG$: diferuloyl monooleoyl glycerol; FDOG: feruloyl dioleoyl glycerol; FMAG: feruloyl monoacylglycerol; $F_2MAG$: diferuloyl monoacylglycerol; and FDAG: feruloyl diacylglycerol.

Example 1

The effect of differing reaction conditions on the production of a PCC was investigated. Ethyl ferulate (EF; ethyl 4-hydroxy-3-methoxy cinnamate) was purchased from Shanghai OSD (Shanghai, China). Novozym 435 (*Candida antarctica* lipase B immobilized on acrylic beads) was obtained from Novozymes North America (Franklinton, N.C.). Soybean oil and Enova diacylglycerol oil (EDO; a product of ADM Kao LLC, Decatur, Ill.) were purchased at a local grocery. All other reagents were from Sigma-Aldrich and Fisher Scientific. Glycerol was spectroscopic grade (<0.1% w/w water). Silica gel (70-325 mesh) and 3-Å molecular sieves were dried at 110° C. under vacuum.

Partially deacylated SBO (PD-SBO) was prepared by treatment of a 2:5 (mol:mol) mixture of 1-propanol and SBO with Novozym 435 (1 g of enzyme per 25 g of substrate) for 2 d at 60° C. on an orbital shaker (200 rpm). Product was filtered to remove enzyme and molecular distilled to remove fatty acid propyl esters, free fatty acids, and residual propanol. The distillation residue fraction (PD-SBO) had a triacylglycerol (TAG) content 50% (w/w) of the original SBO and a very low monoacylglycerol (<5% w/w) content. SBO was emulsified with ethanol at a 1:4 w/w ratio and then treated with Novozym 435 (10:1 w/w substrate to enzyme ratio) at room temperature for 4 h. Enzyme was separated from the product by filtration and excess ethanol was removed by rotary evaporation. 2-MAG was separated from ethyl fatty acid esters by molecular distillation.

Lipids and ferulate species were determined following procedures previously described in an article by Compton et al entitled "Lipase-catalyzed Synthesis of Ferulate Esters" which was published in the Journal of the American Oil Chemical Society, Volume 77, pages 513-519, published in 2000, and incorporated by reference in its entirety herein. Analysis was conducted with a Thermo Separations Products (San Jose, Calif.) HPLC system consisting of a AS3000 autosampler, P4000 pump, SCM1000 solvent degasser, UV6000LP diode array detector, an evaporative light scattering detector (Alltech, Deerfield, Ill.), and a Prodigy C8 column (5 μm, 250×4.6 mm; Phenomenex, Torrance, Calif.).

For the separation of various feruloylated lipids, the column was developed isocratically at 1.5 mL/min with 40:60 (v/v) acetone (containing 1% glacial acetic acid)/acetonitrile. Samples were prepared by 200-fold dilution into acetone and then passage through a Gelman 0.45 μm 13LC PVDF syringe filter prior to injection. The injection volume was 10 μL. The column eluate was monitored at 340 nm. The evaporative light-scattering detector TAG response was calibrated using dilutions of SBO. A linear response was found for the most prominent species (eluting at 9.7 min) over the 1.0 to 5.0 mg SBO/mL.

For the quantitation of FA and EF, a water/methanol gradient elution regime was employed with detection at 325 nm and with the acetone-diluted samples further diluted 20-fold with methanol. Detector response (325 nm, 7 nm bandpass) was calibrated with FA and EF. Responses were linear for both species in the range employed (EF: 50 to 250:M; FA: 2 to 20:M). The sample injection volume was 10 μL.

Transesterification batch reactions were conducted in 50-mL capped, plastic conical tubes containing EF (1.0 g), oil (4.0 g), and Novozym 435 (0.25 g). Tubes were placed upright into an orbital shaker (200 rpm) and incubated at 60° C. Aliquots (100 μL) were removed at timed intervals for analysis by HPLC and UV spectroscopy (325 nm). UV spectroscopy was used to determine the total concentration of feruloyl species in the oil, which was necessary to correct for a small amount of EF absorption to the enzyme support. Details concerning reaction product analysis and the calculation of product yield have been described in an article by Laszlo et al entitled "Packed-Bed Reactor Synthesis of Feruloylated Monoacyl- and Diacylglycerols:Clean Production of a "Green" Sunscreen" published in 2003 in Green Chemistry Volume 5 pages 382-386 which is incorporated by reference herein in its entirety. For this purpose, yield is based on a definition of product as comprising all feruloylated glycerol species containing 0-2 fatty acid acyl groups. Ferulic acid is considered an unwanted by-product. Batch glycerolysis reactions were conducted in 50-mL glass round bottom Schlenk flasks. Silica (200 mg) and glycerol were mixed together, then oil, EF (if needed), and Novozym 435 were added. Flasks were evacuated and sealed under vacuum. Reactions were conducted as described for the transesterification procedure, but with the additional step of re-evacuating the flasks for 5 min following each sampling.

Substrates (i.e., the various oils and EF) and enzyme were equilibrated for at least 7 d in separate sealed containers enclosed with saturated salt solutions or solid adsorbents to establish fixed water activities for transesterification reactions. The corresponding water concentrations in the equilibrated oils are given in Table 1. Water was measured using coulometric Karl Fischer analysis with 70:30 (v/v) Hydranal AG-H/chloroform as the analyte. Reaction components were combined in capped conical tubes and subjected to batch reaction conditions (vide supra).

TABLE 1

| Salt/adsorbent | Water content (μg/g) | | | Water activity |
| --- | --- | --- | --- | --- |
| | SBO | PD-SBO | EDO | |
| 3-Å Sieves | 10 ± 2[a] | 45 ± 1 | 94 ± 8 | ND[b] |
| Silica gel | 64 ± 17 | 179 ± 54 | 331 ± 90 | <0.01 |
| LiBr | 87 ± 4 | 237 ± 4 | 435 ± 13 | 0.06 |
| LiCl | 126 ± 3 | 325 ± 6 | 609 ± 13 | 0.11 |
| $MgCl_2$ | 320 ± 4 | 897 ± 3 | 1756 ± 3 | 0.33 |
| $Mg(NO_3)_2$ | 525 ± 6 | 1535 ± 19 | 3070 ± 70 | 0.53 |

[a] n = 3.
[b] Not defined.

Novozym 435 (32 g) was solvated in SBO under reduced pressure for 30 min, incubated overnight at room temperature, and then transferred to a jacketed chromatography column (2.5×30 cm, 147 mL nominal internal volume). Using β-carotene as a marker, the bed included volume was estimated to be 80 mL. The enzyme bed was conditioned overnight by recirculating SBO at 2 mL/min. The reactor was maintained at 60° C. using a circulating bath. Reactants (EF and vegetable oil) were fed into the top of the reactor using a peristaltic pump at 2 mL/min. Reactor effluent was collected in a small reservoir (30 mL), which was kept under a slow stream of $N_2$ with the contents magnetically stirred, and recirculated back into the packed-bed bioreactor. The reaction mixture was prepared by combining 40 g of EF with 160 g of oil at 60° C. While retaining 18 mL of this solution for the reservoir, the reaction mixture was passed onto the column, discarding the displaced SBO to waste, then directing the reactants back to the reservoir once the reactor was entirely loaded. For SBO glycerolysis, a syringe pump delivered glycerol to the reservoir at fixed rates.

Substrates and enzyme equilibrated to a fixed water activity ($\alpha_w$) were combined (1 g EF, 4 g oil and 0.25 g Novozym 435) and incubated at 60° C. for 24 h. The employed oils were SBO (closed circles), PD-SBO (filled triangles), and EDO (open circles). Experiments were performed in triplicate (error bars represent one standard deviation) and the results are plotted in FIG. 1. It can be observed that $\alpha_w$ has minimal impact on transesterification rates. For SBO, reaction under the lowest $\alpha_w$ condition (equilibrated with molecular sieves) produced the lowest rate while reactions performed at the highest $\alpha_w$ (0.53) were slightly faster (P<0.05). However, for EDO and PD-SBO there was no statistically significant reactivity change over the $\alpha_w$ range examined. These findings indicate that the extent of enzyme hydration does not directly influence the transesterification reaction.

At $\alpha_w \geq 0.06$, detectable quantities of ferulic acid were produced during EF transesterification with the various oils (SBO, EDO, and PD-SBO), although the amount of EF hydrolysis was less than 2% within the time allotted (24 h). EF hydrolysis generally increased with $\alpha_w$ (data not shown), but there were no differences among the oils at a given $\alpha_w$ despite their enormous water content differences (Table 1). Consistent with these observations is the finding that, with the exception of molecular sieve-equilibrated reactants, the water content of the reaction media after 24 h were all lower than their initial values, suggesting that hydrolysis was responsible for lower water concentrations. EF hydrolysis is effectively irreversible under these conditions, however a steady-state (i.e., reversible) level of free fatty acids may be produced during the reaction. A SBO transesterification rate increasing with $\alpha_w$ may arise from the generation of small amounts of MAG and diacylglycerol (DAG) by hydrolysis, if the transesterification reaction is rate limited by the acyl acceptor. Therefore, these findings are consistent with EF/SBO transesterification proceeding in a sequential hydrolysis-transesterification reaction via a ping-pong bi-bi mechanism, while hydrolysis is not required for EF reactions with EDO and PD-SBO.

The slight rise in reactivity with increasing $\alpha_w$ observed here with the transesterification of EF with SBO, and the complete insensitivity to $\alpha_w$ of the reaction using partially deacylated oils (EDO and PD-SBO) as the acyl acceptors, is novel. The EF/oil mixture may have a polarity such that water does not condense on the enzyme. An alternative explanation may be that, unlike the examples given, the rate limiting step is deacylation (transfer of ferulate from the enzyme-ester to glyceride), not acylation (transfer of ferulate from its ethyl ester to the enzyme-ester intermediate).

Figure 1:
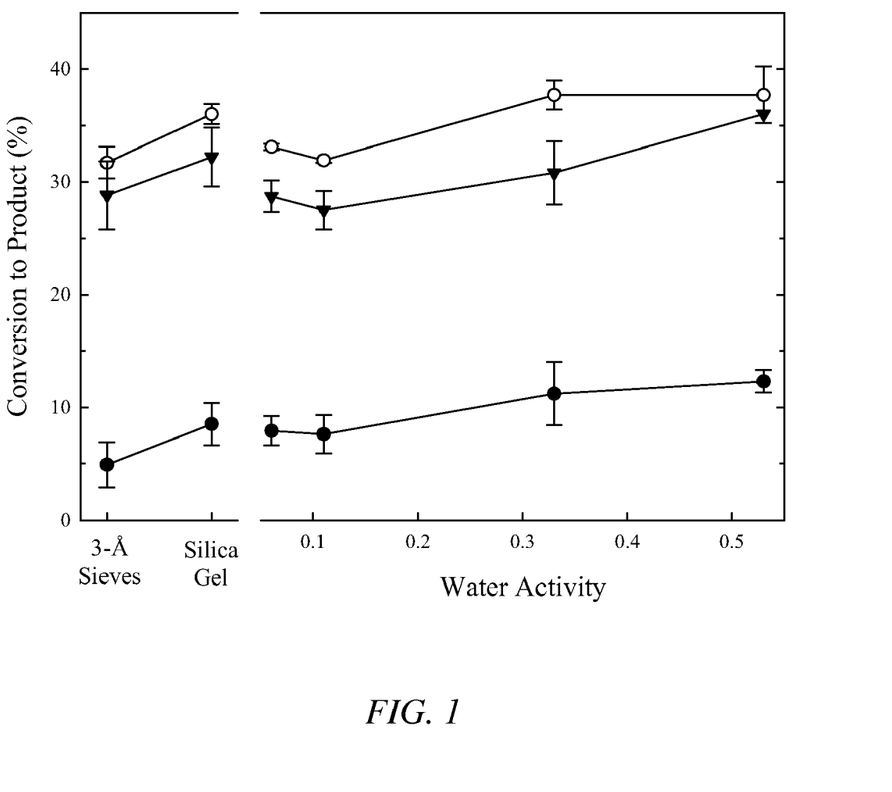
FIG. 1 is a plot illustrating the influence of water activity and various acyl acceptors on the reactivity of *Candida antarctica* lipase B with ethyl ferulate; soybean oil (SBO, closed circles), partially-deacylated SBO (PD-SBO, closed triangles), Enova diacylglycerol oil (EDO, open circles)

Transesterification rates with EF were profoundly affected by the structure of the oil. Reactions with EDO or PD-SBO were 3- to 6-fold faster than with SBO (FIG. 1). Feruloylation of 2-MAG proceeded even faster, achieving a 46±1% product yield in 24 h (cf. 38% for EDO). These observations indicate that the reaction is rate limited by the acyl acceptor, and that oils with free hydroxyl groups are preferred acyl acceptors (better nucleophiles) in comparison with TAG. In these reactions the weight of oil reactants was identical, but their molar concentrations differed slightly. Based on fatty acid composition and glyceride distribution, average molecular weights of 751 and 660 can be estimated for PD-SBO and EDO, respectively. Therefore, the EDO concentration was 14% higher that of PD-SBO. For observations pooled across all $\alpha_w$ values, EDO rates were 13% higher than those of PD-SBO (34.6±2.7 and 30.5±3.4, respectively; P<0.05). The small difference in reactivity observed between EDO and PD-SBO could thus be attributed to differing molar concentrations of the acyl acceptor. However, the higher reactivity of EDO compared to PD-SBO is somewhat counter intuitive as there is the expectation that a free 1(3)-position alcohol would be more reactive than a sn-2-position alcohol in the glycerides. EDO consists approximately of 14 wt % TAG, 57 wt % 1,3-DAG, and 28 wt % 1(3),2-DAG. Therefore, EDO has a 1(3),2-DAG content comparable to PD-SBO (an approximately 50:50 mol % mixture of TAG and DAG, with a unknown distribution between 1,3-DAG and 1(3),2-DAG). A possible explanation for this circumstance is that an enzyme-catalyzed interesterification of EDO to produce free 1(3)-position alcohols occurs rapidly within the time frame of the EF transesterification reaction. Novozym 435 was observed to produce TAG from EDO under these reaction conditions, which demonstrates the potential for enzyme-catalyzed sn-2-position acylation. Non-catalyzed acyl migration may also contribute to 1(3),2-DAG and MAG formation from EDO.

Chemical transesterification of cinnamic acids provides some activation so that they may serve as acyl donors in enzymatic transesterifications. Consequently, it was unanticipated that the reaction of EF with SBO would be deacylation-rate determined.

Example 2

Figure 2:
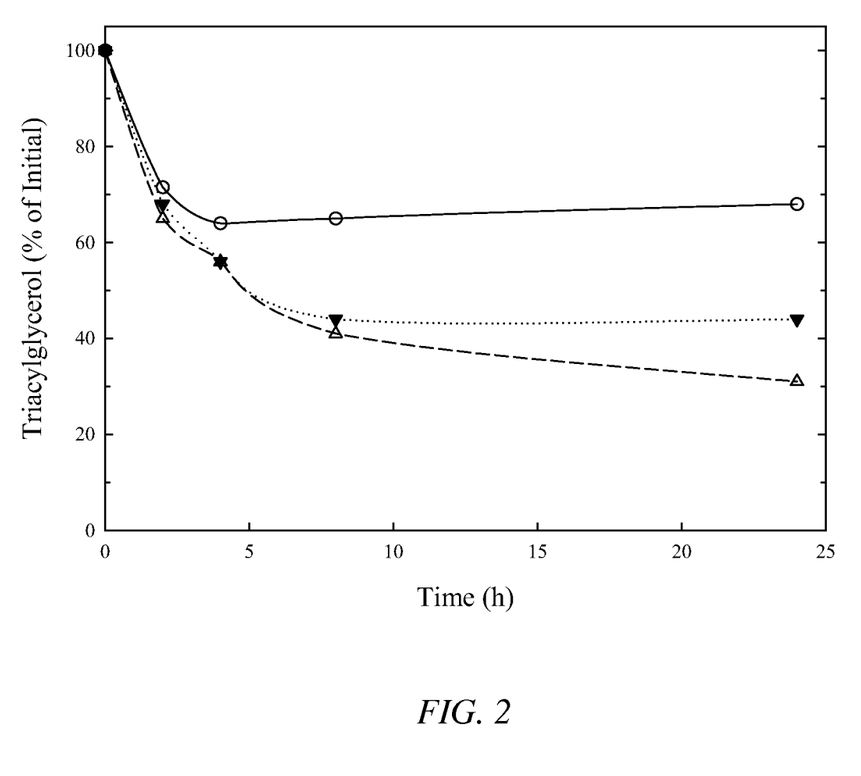
FIG. 2 is a plot showing the degree of SBO glycerolysis by Novozym 435 over time; glycerol/SBO ratios 1:4 (open circles), 1:2 (filled triangles), and 1:1 (open triangles)

The improvement shown in EF transesterification kinetics by using partially deacylated oils in place of SBO suggests that MAG and DAG would be preferable substrates. For commercial considerations, introducing additional processing steps to generate and isolate MAG and DAG has negative consequences. Therefore, in situ MAG and DAG generation from SBO via glycerolysis was examined. FIG. 2 displays the time course for SBO glycerolysis at several glycerol/SBO molar ratios. Glycerol/SBO molar ratios were 1:4 (open circles), 1:2 (filled triangles) and 1:1 (open triangles). Glycerol (92, 184, or 368 mg) was admixed with 200 mg of silica in a flask, and then SBO (4 mL) and Novozym 435 (200 mg) were added. Reactions proceeded under partial vacuum at 60° C. The data in FIG. 2 are mean values of duplicate experiments. The results demonstrate that initial glycerolysis rates were similar for glycerol/SBO molar ratios between 1:4 and 1:1. The residual TAG content at completion was reduced to 64% after 4 h for 1:4 glycerol/SBO, to 44% after 8 h for 1:2 glycerol/SBO, and to 31% after 24 h for 1:1 glycerol/SBO. The percentage of remaining TAG in each case is consistent with that expected for a treatment with a 1,3-specific lipase, i.e., respectively, 64.0%, 44.4% and 25.0% for 1:4, 1:2 and 1:1 glycerol/SBO (14), although CALB is not strictly 1,3-specific. In these experiments, glycerol was adsorbed to silica prior to the introduction of enzyme to avoid fouling the enzyme and its support with excess glycerol, a common practice in the enzymatic production of MAG and DAG from TAG. Keeping the reaction under vacuum minimizes the production of free fatty acids.

Example 3

Figure 3:
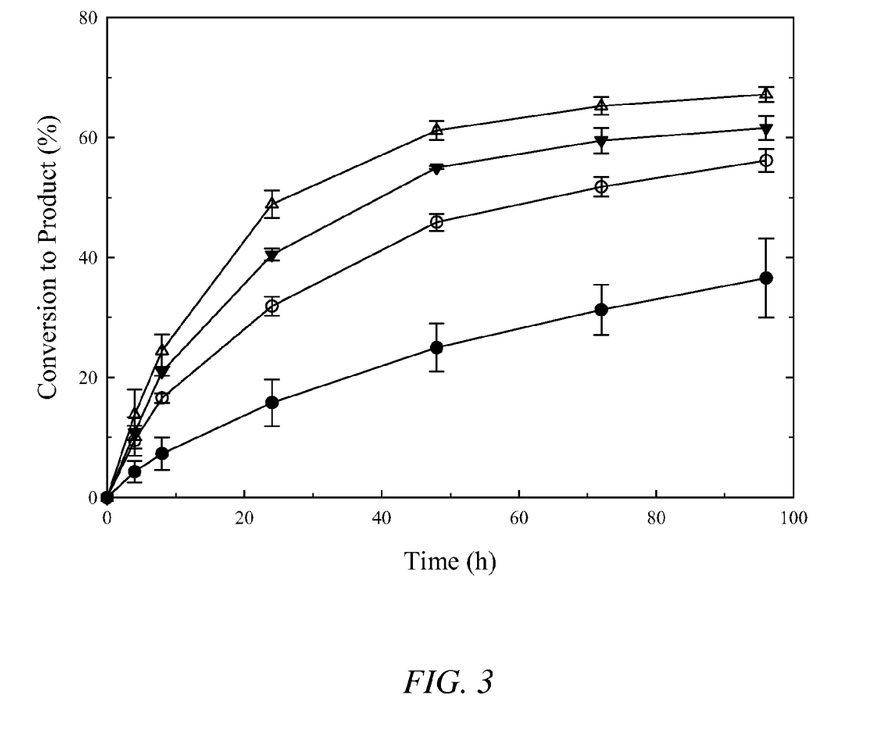
FIG. 3 is a plot showing degree of transesterification over time for SBO with EF in the absence or presence of glycerol; no glycerol (open circles), glycerol/SBO molar ratio 1:4 (filled triangles), 1:2 (open circles), and 1:1 (open triangles)

The effect of the inclusion of silica-adsorbed glycerol to the transesterification reaction of EF with SBO was investigated. The results demonstrate that inclusion of the silica-adsorbed glycerol produced enhanced product formation rates that increased with the amount of added glycerol, as illustrated in FIG. 3. In the FIG. 3 the molar ratio of EF:SBO was 1:1 and the enzyme/substrate ratio (EF+SBO+glycerol) was 1:20 w/w. The reaction contained 200 mg of silica and no glycerol (closed circles), or silica with glycerol at glycerol/SBO molar ratios of 1:4 (filled triangles), 1:2 (open circles) and 1:1 (open triangles). Glycerolysis was conducted for 24 h prior to the addition of EF, which allowed glycerolysis to be complete prior to the start of the EF transesterification (FIG. 2). Reactions proceeded under partial vacuum at 60° C. and were performed in triplicate (error bars represent one standard deviation).

The results demonstrate that during the early phase of EF transesterification (up to 8 h after EF addition), product formation rates with 1:2 and 1:1 glycerol/SBO were the same, approximately 4-fold faster than in the absence of glycerol, but there was greater product formation with 1:1 glycerol/SBO than with 1:2 glycerol/SBO after this initial period. The enhanced product formation found using SBO glycerolysis prior to EF transesterification is consistent with the findings above that partially deacylated MAG and DAG (PD-SBO and EDO) react with EF more quickly than SBO.

Attempts to react glycerol, EF and SBO synchronously produced inconsistent results. Trials using 1:4 glycerol/SBO produced an EF transesterification rate comparable to that depicted in FIG. 3, but at higher glycerol/SBO ratios the enzyme support frequently agglomerated, resulting in significant activity loss. This may have resulted from EF precipitation induced by excess solubilized glycerol. Adding more silica to the reaction did not completely eliminate the agglomeration problem, while the inclusion of such large amounts of silica introduced mixing and sampling problems. Furthermore, it was observed that silica-adsorbed glycerol has drawbacks when attempting to implement large-scale processes. Consequently, stepwise glycerolysis and transesterification were implemented on scale-up.

Example 4

Figure 4:
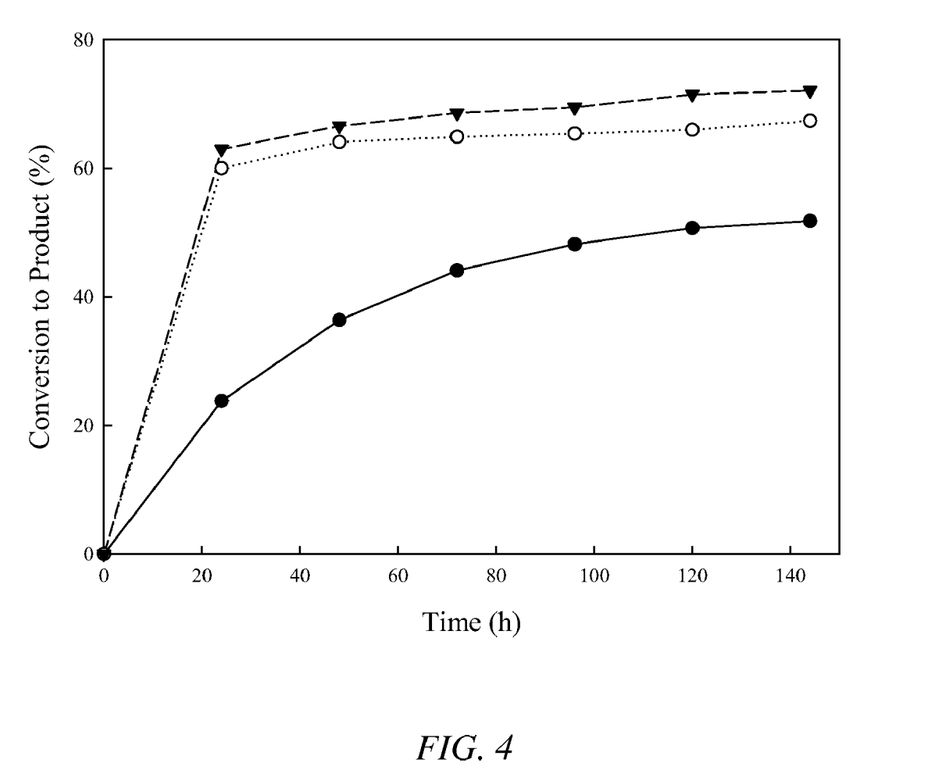
FIG. 4 is a plot comparing packed-bed transesterification s for EF and SBO (closed circles), EDO (open circles), and SBO that had been subjected to glycerolysis (1:1 molar ratio) prior to combination with EF (filled triangles)

A packed-bed bioreactor was investigated as an alternative means of synthesis of the PCC. A packed bed bioreactor represents a practical alternative to batch reactions for utilization of expensive immobilized enzyme. FIG. 4 compares product yields over time with SBO, EDO and glycerolized SBO (1:1 glycerol/SBO mol ratio), using a packed-bed reactor. As expected, compared to TAG there was a pronounced increased in reactor performance using the partially deacylated oils. Due to a lower substrate:enzyme ratio, packed-bed conversions were faster than those observed in batch reactions, see FIG. 3. Glycerolized SBO was conveniently generated using Novozym 435 in a packed bed by slowly metering in glycerol over a 24-h period. By this method the same extent of SBO TAG conversion (70%) to MAG and DAG was achieved as that obtained in a batch reactor (FIG. 2, 1:1 glycerol/SBO mol ratio). These observations indicate that a facile two-step process, SBO glycerolysis followed by EF transesterification, can be implemented in a packed-bed reactor without relying on glycerol-adsorbed silica. The mixture of MAG and DAG from SBO glycerolysis are much more reactive than SBO during EF transesterification, which leads to greater reactor productivity.

Example 5

An HPLC method using a water/methanol gradient and a phenyl-hexyl reverse-phase column was investigated to elucidate the molecular species of biocatalytically derived feruloylated vegetable oils.

Glycerol (0.0 to 0.368 g, 0.0 to 4.2 mmol) was blended with 200 mg of silica gel in 50-mL Schlenk flasks. Triolein (3.54 g, 4.0 mmol) and Novozym 435 (0.221 g) were added to the Schlenk flasks and the mixtures were degassed under vacuum for 30 min. The evacuated flasks were shaken on an orbital shaker (200 rpm) at 60° C. for 24 h. EF (0.888 g, 4.0 mmol) was added the flasks, and the flasks were evacuated for 5 min. The reaction mixtures were allowed to shake (200 rpm) at 60° C. for 120 h. Aliquots (100 µL) were removed at timed intervals for analytical HPLC and UV spectroscopy (325 nm). The flasks were evacuated for 5 min after each sampling. The feruloyl mono- and dioleoyl glycerol (FMOG and FDOG, respectively) and the diferuloylated monooleoyl glycerol ($F_2$MOG) species were characterized by HPLC-MS.

After reaching equilibrium (120 h), the feruloylated oleoylglycerol reaction mixtures were extracted with 10 mL of 2-methyl-2-propanol. The solutions were filtered to remove the Novozym 435 and silica gel. The solids were rinsed with two 2-mL portions of 2-methyl-2-propanol. The combined filtrates (14 mL) were transferred to 50-mL Schlenk flasks. Water (1.0 g, 55.0 mmol) and Lipase PS-C "Amano" I (0.100 g) were added to the flasks, and the flasks were shaken (175 rpm) at 37° C. Aliquots (20 µL) were removed at timed intervals for analytical HPLC and UV spectroscopy (325 nm).

The packed-bed bioreactor synthesis of feruloylated SBO is described in the article by Laszlo et al. entitled Packed-Bed Bioreactor Synthesis of Feruloylated Monoacyl- and Diacylglycerols: Clean Production of a "Green" Sunscreen and previously incorporated herein. A solution of EF (40 g) dissolved in SBO (160 g) at 60° C. was circulated over a bed of Novozym 435 (34 g) at 60° C. for 144 h. The reaction progress was monitored by analytical HPLC. Byproducts and unreacted staring material were removed from the reaction mixtures by molecular distillation at 120° C. The biocatalytic conversion of ethyl ferulate (EF) and soybean oil (SBO) results in a mixture of feruloyl-MAG (FMAG), feruloyl-DAG (FDAG), and diferuloyl-MAG ($F_2$MAG), as well as trace amounts of feruloyl glycerol (FG) and diferuloyl glycerol ($F_2$G). Analysis (HPLC-MS and NMR) confirmed that diferuloyl derivatives of glycerol are produced.

Feruloylated SBO (240 g) and water (14.5 g) were dissolved in 250 mL of 2-methyl-2-propanol in a 1-L Fernbach flask. The solution was shaken (125 rpm) at 37° C. for 144 h. Aliquots (100 µL) were removed at timed intervals for analytical HPLC and UV spectroscopy (325 nm). The feruloyl glycerols (FG and $F_2$G) were isolated by preparative HPLC. The 40 aliquots corresponding to the FG collected during HPLC separations were combined and the solvent removed under vacuum at 40° C. to yield a cloudy, colorless viscous oil. The isolated FG was analyzed by analytical HPLC and was found to be pure. Yield: 3.69 g. $^1$H NMR ($d_6$-acetone): δ (ppm) 7.60 (1H, d, J=16.1 Hz, H-8), 7.31 (1H, s, H-2), 7.12 (1H, d, J=8.2 Hz, H-6), 6.85 (1H, d, J=8.1 Hz, H-5), 6.37 (1H, d, J=16.1 Hz), 4.19 (2H, dm, J=24.3 Hz, H-11), 3.90 (3H, s, H-7), 3.87 (1H, m, H-12), 3.58 (2H, m, H-13). $^{13}$C{$^1$H} NMR ($d_6$-acetone): δ (ppm) 167.5 (C-10), 150.1 (C-4), 148.8 (C-3), 145.8 (C-8), 127.5 (C-1), 123.9 (C-6), 116.1 (C-5), 115.8 (C-9), 111.3 (C-3), 71.0 (C-12), 66.3 (C-13), 64.1 (C-11), 56.3 (C-7). APCI MS: 266.9 [M-H]$^-$ (calcd $C_{13}H_{16}O_6$: 268.1).

The 40 aliquots corresponding to the $F_2$G collected during preparative HPLC separations were combined and the solvent removed under vacuum at 40° C. to yield a viscous, yellow oil. The isolated $F_2$G was analyzed by analytical HPLC and was found to be pure. Yield: 2.3 g. 1H NMR ($d_6$-acetone): δ (ppm) 7.62 (2H, d, J=16.1 Hz, H-8), 7.30 (2H, s, H-2), 7.10 (2H, d, J=6.9 Hz, H-6), 6.85 (2H, d, J=6.5 Hz, H-5), 6.40 (2H, d, J=16.1 Hz), 4.27 (4H, m, H-11), 4.18 (1H, m, H-12), 3.88 (3H, s, H-7). $^{13}$C{$^1$H} NMR ($d_6$-acetone): δ (ppm) 167.4 (C-10), 150.1 (C-4), 148.8 (C-3), 146.1 (C-8), 127.4 (C-1), 124.0 (C-6), 116.1 (C-5), 115.6 (C-9), 111.4 (C-3), 68.35 (C-12), 66.0 (C-11), 56.4 (C-7). APCI MS: 464.9 [M-H+Na], 443.0 [M-H]$^-$ (calcd $C_{23}H_{24}O_9$: 444.14).

High performance liquid chromatography (HPLC) incorporating ultraviolet (UV) detection, electronic light scattering (ELS) detection, and mass spectrometry (MS methods were used to resolve TAG species based on fatty acid composition, positional isomers, and degree of unsaturation. The biocatalytic and chemical conversion of TAG to structured lipids and fatty acid esters resulted in intermediate DAG and MAG as well as FFA. We developed HPLC methods to resolve the DAG and MAG and to elucidate the positional isomers of these intermediate glycerols.

The biocatalytic conversion of ethyl ferulate (EF) and soybean oil (SBO) results in a mixture of feruloyl-MAG (FMAG), feruloyl-DAG (FDAG), and diferuloyl-MAG ($F_2$MAG), as well as trace amounts of feruloyl glycerol (FG) and diferuloyl glycerol ($F_2$G). To help identify these species chromatographically, model reactions of EF and triolein were examined to lessen the convolution of the HPLC chromatograms due to the multiple fatty acids in SBO.

Analyses were performed using a Thermo Separation Products (San Jose, Calif.) HPLC system consisting of a Spectra System AS3000 autosampler, a Spectra System P4000 pump, a Spectra System UV6000LP detector, an Alltech (Deerfield, Ill.) 500 Evaporative Light-Scattering Detector (ELSD), and a Luna Phenyl-Hexyl column (5 µm, 250×4.6 mm, Phenomenex, Torrance, Calif.). Solvents were filtered using Whatman 0.45 µm nylon membrane filters (Sigma-Aldrich) and degassed using a Thermo Separation Products SCM 1000 Membrane Degasser. The feruloylated lipid species were determined using a three-solvent gradient. Solvent A was water (268 mL), methanol (70 mL), 1-butanol (11 mL), and glacial acetic acid (1 mL). Solvent B was water (93 mL), methanol (245 mL), 1-butanol (33 mL), and glacial acetic acid (3 mL). Solvent C was methanol. The column was developed at 1.0 mL/min with a 5 min isocratic flow of 3:1 A:B, a 2 min linear gradient to 100% B, a 5 min isocratic flow of 100% B, a 2 min linear gradient to 100% C, a 13 min isocratic flow of 100% C, followed by a 3 min linear gradient to 3:1 A:B. The UV detector response (325 nm, 7 nm bandpass) was calibrated with EF. Injection volumes were 10 µL. HPLC-MS. HPLC-atmospheric pressure chemical ionization MS (HPLC-APCIMS) was conducted with a Finnigan-Thermoquest LCQ LC-MS system (AS3000 autoinjector, P4000 HPLC pump, UV6000 PDA detector, LCQ ion-trap mass spectrometer and a nitrogen generator) (San Jose, Calif.) all running under the Xcaliber 1.3 software system. The MS was run with the electrospray ionization (ESI) interface operating in the negative ion mode. The source inlet temperature was set at 220° C. and the sheath gas rate was set at 90 arbitrary units. The MS was optimized by using the autotune feature of the software while infusing a solution of $F_2G$ in with the effluent of the column and tuning on an atomic mass unit of 531 $[M-H]^-$. The software package was set to collect mass data between 100-1500 atomic mass units (AMUs). Generally the most significant sample ions generated under these conditions were $[M-1]^-$. The LC conditions were the same as those described above for the analytical system, with the liquid flow exiting the diode array detector was split 1/10 with the low flow split being directed into the ESI-MS interface.

In contrast to HPLC methods that have been developed previously for the resolution of phenolic lipids, which have focused on catecholic (e.g. urushiol, anacardic, ginkgolic), resorcinolic, and hydroquinonic lipids, the present method provides an HPLC method that is effective for the separation and identification of various phenolic substituted MAG and DAG species.

Example 6

Preparative HPLC was used to isolate FG and $F_2G$. A Shimadzu (Columbia, Md.) preparative HPLC system was used with dual 8 A pumps, SIL 10 vp autoinjector, SPD M10 Avp photodiode array detector, and a SCL 10 Avp system controller, all operating under the Shimadzu Class VP operating system. Sample aliquots (2 mL) in 1% acetic acid in acetone were injected on a Waters (Milford, Mass.) Bondapak C18 PrepPak column (15-20 uM, 125 Å, 47 mm×300 mm) in a radial compression module. The column was prequilibrated with 1% acetic acid, 10% acetonitrile and 89% acetone at a flow rate of 50 mL/min, and the effluent was monitored at 360 nm. The column was developed to 23% acetonitrile over 10 minutes. Peaks were collected by hand. The procedure was repeated 40 times to obtain sufficient quantities of purified FG and $F_2G$.

Example 7

Analyses were carried out in order to differentiate of mono- and diferuloylated acylglycerols. Feruloylated SBO was enzymatically hydrolyzed with an excess of water in 2-methyl-2-proanol solutions at 37° C. using a sn-1,3 specific enzyme, Lipase PS-C "Amano" I, which showed no substrate activity towards the feruloyl moiety as described in the article by Compton et al previously incorporated herein. The deacylation was facile and reached equilibrium after 48 h. Unexpectedly, the deacylation of the feruloylated SBO resulted in two feruloylated glycerol species, one of which had not been detected by our original water/methanol or acetone/acetonitrile HPLC methods. The isolation of the two feruloylated glycerol species by preparative HPLC was achieved using an isocratic development of a C18 column with an amended acetone/acetonitrile solvent system. $^1$H NMR analysis of the isolated oils allowed for the unambiguous identification of 1(3)-feruloyl-sn-glycerol (FG) and 1,3-diferuloyl-sn-glycerol ($F_2G$). The FG spectrum consisted of three unique sets of glycerol protons in a 2:1:2 ratio (H-8 11:H-12:H-13), indicating a sn-1(3) substitution of the glycerol backbone. The ratio of the feruloyl methyl peak (H-7) to the glycerol protons confirmed a single feruloyl moiety on the glycerol. The $F_2G$ spectrum showed two sets of glycerol protons (H-11:H-12) in a 4:1 ratio, consistent with sn-1,3 substitution pattern. The ratio of the feruloyl methyl peak (H-7) to the glycerol protons confirmed two feruloyl moieties on the glycerol. The identification of the FG and $F_2G$ was also confirmed by HPLC-MS. The unexpected discovery of $F_2G$ species indicates that a significant quantity of the $F_2MAG$ is produced during the transesterification of the SBO with the EF. However, previous HPLC-MS methods did not reveal the presence of any diferuloylated acylglycerol species. Therefore, a new HPLC-MS method was developed to better separate and identify the feruloyl and diferuloyl acylglycerol species.

Figure 5:
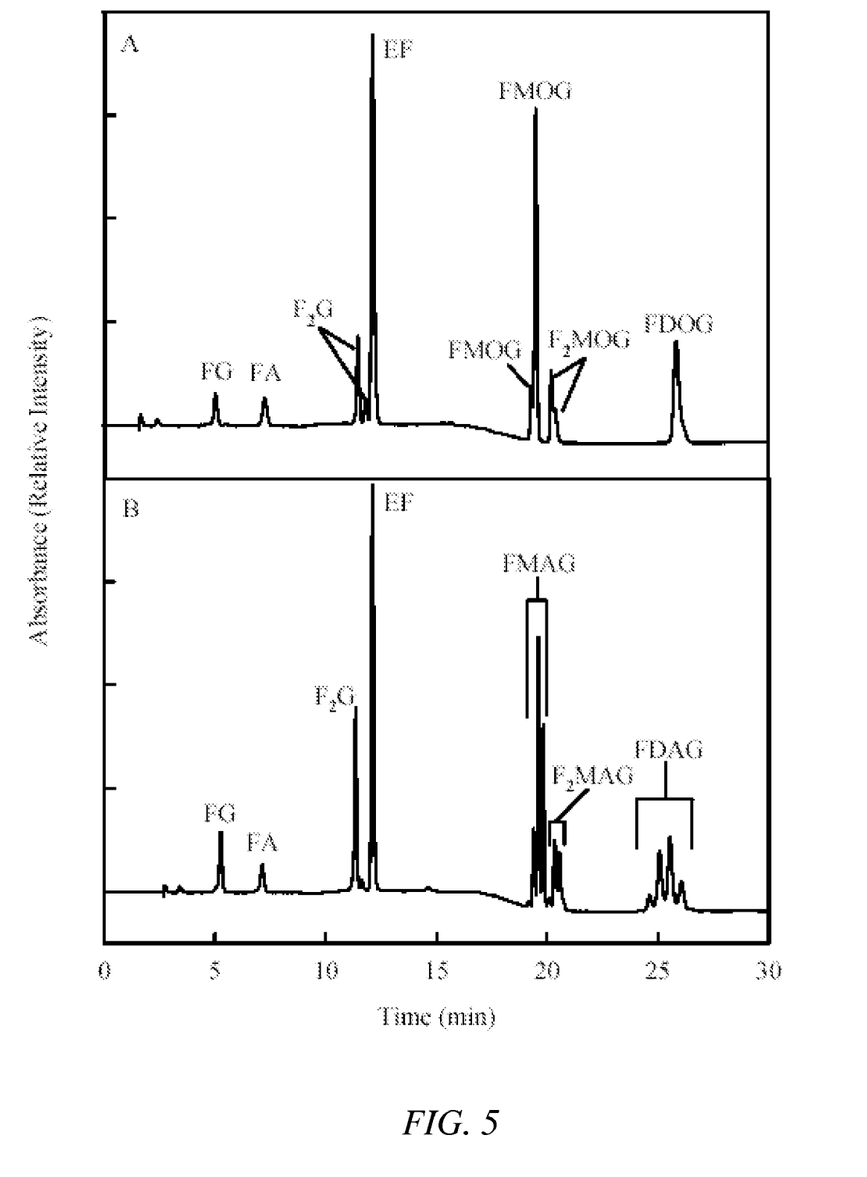
FIG. 5 consists of two plots of analytical HPLC chromatograms of the transesterification reaction mixtures of A) triolein, EF and glycerol (2:2:1 mol ratio) and B) SBO and EF (1:1 mol ratio) after 144 h at 60° C. catalyzed by *Candida. antarctica* lipase B (Novozym 435; EF: ethyl ferulate, FG: feruloyl glycerol, $F_2G$: diferuloyl glycerol, FMOG: feruloyl monooleoylglycerol, $F_2MOG$: diferuloyl monooleoylglycerol, FDOG: feruloyl dioleoylglycerol, FMAG: feruloyl monoacylglycerol, $F_2MAG$: diferuloyl monoacylglycerol, FDAG: feruloyl diacylglycerol.

The transesterification of SBO with EF resulted in a mixture of feruloylated acylglycerol species, some of which have not been previously identified and contain two feruloyl groups per glycerol backbone. A new HPLC method based on a previously used water/methanol solvent system but using a phenyl-hexyl column instead of a C8 column and an amended gradient sequence was developed to separate the feruloylated acylglycerols. The new method was effective in separating the FG and $F_2G$ from the FA and residual EF (FIG. 5). These species were identified in the chromatogram using FA and EF standards and the FG and $F_2G$ that were purified by preparative HPLC (discussed previously). The FMAG and FDAG regions ($R_t$=18 to 27 min), however, were convoluted with peaks due to the multiple fatty acids in SBO, making the assignment of the diferuloylated species ambiguous.

To deconvolute the HPLC chromatogram and simplify the MS analysis of the feruloylated species, the transesterification of triolein with EF was investigated as a model reaction. The enhancement of the transesterification kinetics of EF with SBO catalyzed by C. antarctica lipase B using glycerol as a co-reactant is described herein. Accordingly, the present transesterifications of triolein with EF were performed in the presence of glycerol. The chromatograph of the reaction of a 2:2:1 ratio of EF:triolein:glycerol after reaching equilibrium (120 h) is shown in FIG. 1A. The FG, FA, $F_2G$ and EF were identified using standards as described above. The remaining peaks were identified by HPLC-APCIMS in the negative ion mode. Table 2 lists the peaks obtain by HPLC-MS chromatography and their corresponding $R_t$ and major ions. The identification of the FG and $F_2G$ isolated by preparative HPLC and characterized by $^1$H and $^{13}$C NMR spectroscopy was confirmed by MS. The major ion of the $F_2G$ species was 23 mass units greater than its calculated exact mass, which corresponds to the addition of a $Na^+$ atom to the negative $F_2G$ ion. Ion contaminants from salts (e.g. $Na^+$ and $Li^+$) often form adducts with the major ion.

TABLE 2

| Species[a] | $R_t$ (min)[b] | Exact Mass | Major Ion (m/z)[c] | Peak Area (%)[a] |
|---|---|---|---|---|
| FG | 6.7 | 268.1 | 266.9 [M − H]$^-$ | 8.2 |
| FMOG | 18.5 | 532.3 | 531.1 [M − H]$^-$ | 29.6 |
| FDOG | 25.3 | 796.6 | 795.3 [M − H]$^-$ | 11.7 |
| $F_2G$ | 11.1 | 444.1 | 464.9 [M − H + Na] | 13.8 |

TABLE 2-continued

| Species[a] | $R_t$ (min)[b] | Exact Mass | Major Ion (m/z)[c] | Peak Area (%)[a] |
|---|---|---|---|---|
| $F_2G$[d] | 11.4 | 444.1 | 465.0 [M − H + Na] | 0.6 |
| $F_2MOG$ | 20.2 | 708.1 | 714.3 [M − H + Li] | 1.1 |
| $F_2MOG$[d] | 20.2 sh[e] | 708.1 | 707.1 [M − H]⁻ | 0.9 |

[a] Feruloylated species obtained after the enzyme catalyzed reaction of 2:2:1 mole ratio of EF:triolein:glycerol at 60° C. (144 h). The percent peak area of the species related to the total peak area of all feruloylated species, including FA and EF, as detected by HPLC using the UV detector (325 nm). See FIG. 1 caption for acronym definitions.
[b] Retention times were determined using the UV6000 detector (325 nm) during HPLC-MS.
[c] Major ions detected by HPLC-MS in negative ion mode.
[d] sn-1,2-diferuloyl positional isomers.
[e] Shoulder.

The presence of the previously undetected $F_2MOG$ species was confirmed by HPLC-MS using the new phenyl-hexyl column method. The $F_2MOG$ eluted as a single peak ($R_t$ 20.2 min, FIG. 5A) with the expected mass (Table 2) followed by a small shoulder. The major ion detected for the shoulder also corresponded to the mass for $F_2MOG$. Other evidence suggests that Novozym 435 shows preferential sn-1(3)-positional acylation under our transesterification conditions. Thus, it was assumed that the major $F_2MOG$ peak corresponded to the 1,3-diferuloyl-2-oleoyl-sn-glycerol isomer, while the shoulder was the less abundant 1,2-diferuloyl-3-oleoyl-sn-glycerol. Similarly, the other diferuloyl species, $F_2G$, eluted as two peaks with the same mass. The larger peak ($R_t$ 11.1 min, FIG. 5A) was identified by the $F_2G$ standard isolated by preparative HPLC and was confirmed by ¹H NMR to be the 1,3-diferuloyl-sn-glycerol (see above). Thus, the less abundant peak was assumed to be 1,2-diferuloyl-sn-glycerol. Therefore, it can be concluded that the sn-1,3-diferuoyl isomers elute before the sn-1,2-diferuloyl isomers, further suggesting that the larger $F_2MOG$ peak was the 1,3-diferuloyl-2-oleoyl-sn-glycerol. The potential for Novozym 435 to catalyze the acylation of the sn-2-position and the non-catalyzed acyl migration, accounting for the formation of a small quantity of sn-2-feruloyl-substituted acylglycerols, is discussed elsewhere herein.

The previously known FMOG species eluted as a small shoulder preceding a single peak ($R_t$ 18.5 min, FIG. 5). The main peak possessed a major ion of the expected mass, but the MS data for the shoulder was inconclusive. It was believed, however, that the shoulder was also a FMOG isomer. Again, evidence supporting that C. antarctica lipase B's preferentially esterifies the sn-1(3)-position under our transesterification conditions suggests that the feruloyl group of the various monoferuloyl acylglycerol species occupies the sn-1(3)-position. The hydrolysis of the feruloylated oleoylglycerols offered insight into which FMOG positional isomer, the 1-feruloyl-3-monooleoyl-sn-glycerol or 1-feruloyl-2-oleoyl-sn-glycerol, corresponded to the shoulder and to which corresponded the main peak. Consider the transesterification of triolein with EF without glycerol, which produced the highest FDOG to FMOG ratio (Table 23). The FDOG, 1-feruloyl-dioleoyl-sn-glyerol, when hydrolyzed by the predominantly sn-1,3 specific B. cepacia lipase, which showed no activity towards the feruloyl moiety, would be expected to yield 1-feruloyl-2-oleoyl-sn-glycerol. The HPLC chromatogram of the hydrolyzed reaction mixture after 24 h (data not shown) showed a large increase in the FMOG shoulder ($R_t$ 18.5) and complete consumption of the FDO. This strongly suggests that the FMOG shoulder was the 1-feruloyl-2-oleoyl-sn-glycerol isomer. Thus, the FMOG main peak was designated as the 1-feruloyl-3-oleoyl-sn-glycerol isomer. The FMOG main peak was essentially consumed within 24 h under the hydrolysis conditions and would be expected to be converted to FG. Indeed, the FG peak increased relative to the FMOG main peak's consumption, further supporting that the FMOG main peak was the 1-feruloyl-3-oleoyl-sn-glycerol. The results presented above show that the phenyl-hexyl HPLC-MS column method allowed for the separation and unambiguous identification of the various feruloylated and diferuloylated oleoylglycerols and their positional isomers formed during the transesterification of triolein with EF. Although the many feruloylated acylglycerols formed during the transesterification of SBO with EF (Rt 18.0 to 28.0 min, FIG. 5B) cannot be as cleanly separated using the phenyl-hexyl HPLC-MS column method due to SBO's multiple fatty acids, the results from the triolein transesterification s can be used to assign the peaks to classes of feruloylated SBO glycerols. FIG. 5B shows that the FMAG, $F_2MAG$ and FDAG elute at similar times to their corresponding feruloylated oleoylglycerols. This allowed for quantification of the three groups of feruloylated acylglycerols, which was not possible using previous HPLC methods.

TABLE 3

| | | Species Distribution (%)[a] | | | | | | | |
|---|---|---|---|---|---|---|---|---|---|
| Trial | triolein:EF:glycerol (mole ratio) | FG (6.7)[b] | $F_2G$ (11.1) | $F_2G$ (11.4) | FMOG[c] (18.5) | FMOG (18.5) | $F_2MOG$ (19.2) | $F_2MOG$[c] (19.2) | FDOG (25.3) |
| A | 1:1:1 | 18.6 | 12.2 | 0.3 | 4.0 | 32.5 | 0.9 | 0.6 | 7.5 |
| B | 2:2:1 | 8.2 | 13.8 | 0.6 | 3.9 | 29.6 | 1.1 | 0.9 | 11.7 |
| C | 4:4:1 | 3.0 | 15.7 | 0.6 | 3.0 | 21.7 | 2.3 | 1.1 | 16.0 |
| D | 1:1:0 | 0.4 | 6.2 | 0.0 | 1.1 | 11.0 | 8.2 | 0.0 | 19.7 |

[a] The species distributions were determined as the percent peak area of the species related to the total peak area of all feruloylated species, including FA and EF, as detected by HPLC using the UV detector (325 nm). See Section [0016] for acronym definitions.
[b] The $R_t$ (min) corresponding to the peaks in FIG. 5A.
[c] Shoulder to the main peak (see FIG. 5A).

Example 8

Figure 6:
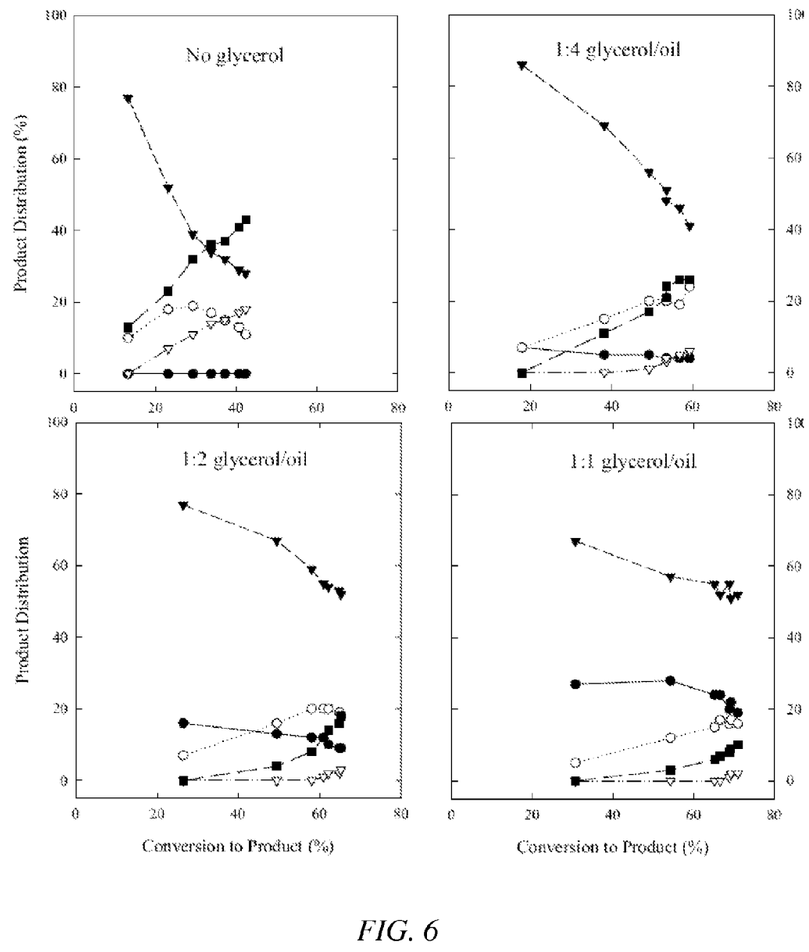
FIG. 6 consists of four plots showing the product distributions during the transesterification of glycerolized triolein (triolein interesterified with glycerol) with EF using Novozym 435 over the course of 144 h; FG (filled circles), $F_2G$ (open circles), FMOG (closed triangles), $F_2MOG$ (open triangles), FDOG (closed squares), see FIG. 5 caption for acronym definitions.

The transesterification kinetics of triolein or SBO with EF catalyzed by C. antarctica lipase B can be enhanced by performing a glycerolysis of the triolein prior to the addition of EF. The influence of the glycerol:triolein mole ratio on the distribution of the feruloylated oleoylglycerols and feruloyl glycerols during transesterification s catalyzed by Novozym 435 over the course of 144 h at 60° C. was examined. The highest glycerol:triolein ratio (1:1) resulted in the most EF converted to total product, 71%, while the absence of glycerol resulted in the lowest conversion, 42%, as shown in FIG. 6. Not only does the pre-glycerolysis of the triolein influence the overall conversion to products, the distribution of feruloylated products was also greatly influenced. For the discussion of product distributions as influenced by the glycerol:triolein ratios, the two positional isomers for each of $F_2G$, FMOG, and $F_2MOG$ were summed when reporting the percent conversion of each species. FIG. 6 shows the distribution of the feruloylated oleoylglycerols and feruloyl glycerols related to the total amount of feruloylated species formed, excluding ferulic acid. The most abundant species initially at all ratios was FMOG. This indicated that monooleoylglycerol formed before the addition of EF was the most reactive oleoylglycerol species towards the EF. Even without the addition of glycerol, FMOG is the most abundant species after 8 h. This also suggested that the triolein must be deacylated prior to transesterification with the EF. Indeed, contrary to expectations, it appears that the rate-limiting step of the transesterification of triolein with EF is the deacylation of the triolein to provide reactive sites on the glycerol backbone and not the subsequent transesterification of the EF to the glycerol. The kinetics of the sequential hydrolysis-transesterification (ping-pong bi-bi mechanism) of the triolein/EF transesterification is discussed in detail above.

The pre-glycerolysis of the triolein most greatly influenced the FDOG:FMOG ratio after 144 h. As the glycerol:triolein ratio was increased the amount of FDOG decreased from 43% with no glycerol to 10% with 4:1 glycerol:triolein. Concurrently, the amount of FMOG increased from 28 to 52% after 144 h. This was expected since the pre-glycerolysis provides more of the reactive monooleoylglycerol species and lowers the probability that a fatty acid group was available for transesterification to the free site of the FMOG to form FDOG. The most perplexing phenomenon observed during the transesterification was the amounts of $F_2G$ formed at early percent conversions. The formation of both FG and $F_2G$ was easily explained when EF is added to glycerolized triolein, since residual glycerol is present. The residual glycerol and the deacylation of the mono- and dioleoylglycerol during the subsequent transesterification with EF can account for the larger quantities of $F_2G$ formed during these reactions. When triolein is used for the transesterification with EF, however, a substantial amount of $F_2G$ is initially formed, 10%. The pathway from triolein and EF to $F_2G$ most likely proceeded through a FMOG intermediate that was subsequently deacylated, and the fatty acid replaced by a second feruloyl group. FMOG most likely serves as the intermediate for some of the other feruloylated oleoylglycerols. The newly described phenyl-hexyl HPLC-MS method sufficiently separated and allowed for the identification and quantification of the triolein/EF transesterification products. The interaction of the feruloyl moieties with the phenyl groups of the phenyl-hexyl column in reverse phase allows for the better separation of the feruloylated acylglycerols than can be obtained with a typical reverse phase C8 or C18 column.

The present disclosure provides methods to identify and monitor these contaminates during synthesis and purification. Further, the present invention provides methods for carrying out lipase-catalyzed reactions that provide increased reaction rates and thus increased commercial efficiency in the production of the desired products. The methods disclosed herein make possible enhanced product quality and potential energy/environmental savings in the context of immobilized lipase technology.

While preferred embodiments of the invention have been shown and described, modifications thereof can be made by one skilled in the art without departing from the spirit and teachings of the invention. The embodiments described herein are exemplary only, and are not intended to be limiting. Many variations and modifications of the invention disclosed herein are possible and are within the scope of the invention. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, etc.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the preferred embodiments of the present invention. The discussion of a reference in the Description of Related Art is not an admission that it is prior art to the present invention, especially any reference that may have a publication date after the priority date of this application. The disclosures of all patents, patent applications, and publications cited herein are hereby incorporated by reference, to the extent that they provide exemplary, procedural or other details supplementary to those set forth herein.

What is claimed is:

1. A composition comprising a compound having a formula I:

wherein:
at least one of $X_1$ and $X_2$ is present; $X_1$ and $X_2$ are the same or different; at least one of $X_1$ or $X_2$ has at least one UV-absorbing chromophore; and $b+f\geq 2$;
at least one of $X_3$ and $X_4$ is present; $X_3$ and $X_4$ are the same or different and are selected from the group consisting of a moiety characterized by the formula: —CH=CH—$(CH_2)_n CH_3$ where n ranges from 8 to 24; a moiety characterized by the formula: —NCO—$(CH_2)$—CH=CH—$(CH_2)_7 CH_3$; a sphingosine; a ceramide; and combinations thereof;
Y comprises an O, N, or S that is substituted or unsubstituted;
each a, b, c, e and f is $\geq 0$ and $a+b+c+e+f\geq 2$;
d is 0 or 1;
n1, n2, n3, n4, n5, and n6 represent the number of hydrogen atoms required to complete the undesignated valencies; and
m ranges from 1 to 100 and each individual m unit is the same or different.

2. The composition of claim 1 wherein the compound having at least one UV-absorbing chromophore is a phytochemical.

3. The composition of claim 2 wherein the phytochemical has a carboxyl containing group.

4. The composition of claim 1 having anti-aging properties, anti-neoplastic properties, antibacterial properties, antioxidant properties, or combinations thereof.

5. The composition of claim 2 wherein the phytochemical is selected from the group consisting of an aromatic species, an unsaturated isoprenoid, an unsaturated terpenoid, a hindered hydroxy-substituted cinnamic acid, and an unhindered hydroxy-substituted cinnamic acid.

6. The composition of claim 2 wherein the phytochemical is selected from the group consisting of maleanilic acid, homovanillic acid, folic acid, crocetin, coumaric acid, caffeic acid, ferulic acid, and sinapic acid (sinapinic acid).

7. The composition of claim 1 wherein the $X_3$, $X_4$ or both are selected from the group consisting of a sphingosine, a ceramide and combinations thereof.

8. The composition of claim 1 wherein the $C_a$-$C_b$-$C_c$—$(Y)_d$—$C_e$-$C_f$ portion of formula I is a sphingosine or a ceramide.

9. The composition of claim 1 wherein $X_1$ or $X_2$ is ferulic acid and the ferulic acid provides the at least one UV-absorbing chromophore.

10. The composition of claim 1 wherein $X_1$ and $X_2$ are ferulic acid and the ferulic acid provides the at least one UV-absorbing chromophore.

11. The composition of claim 9 wherein $X_1$, $X_2$, or both are ferulic acid and the ferulic acid provides the at least one UV-absorbing chromophore.

12. A product for topical application comprising the composition of claim 1.

13. A product comprising the composition of claim 1, wherein the product is a lotion, a sunscreen, a cosmetic product, an agrochemical, a pharmaceutical, a nutritional product or combinations thereof.

14. The composition of claim 5 wherein the $C_a$-$C_b$-$C_c$—$(Y)_d$—$C_e$-$C_f$ portion of formula I is a sphingosine or a ceramide.

15. The composition of claim 5 wherein $X_1$ or $X_2$ comprises ferulic acid and the ferulic acid provides the at least one UV-absorbing chromophore.

16. The composition of claim 14 wherein $X_1$ or $X_2$ comprises ferulic acid and the ferulic acid provides the at least one UV-absorbing chromophore.

17. A product comprising the composition of claim 5, wherein the product is a lotion, a sunscreen, a cosmetic product, an agrochemical, a pharmaceutical, a nutritional product or combinations thereof.

18. A product containing the composition of claim 5, wherein the composition has at least two different compounds having the formula I, wherein the product is a lotion, a sunscreen, a cosmetic product, an agrochemical, a pharmaceutical, a nutritional product or combinations thereof.

19. A composition comprising a compound having a formula I:

wherein:
at least one of $X_1$ and $X_2$ is present; and $X_1$, $X_2$, or both are ferulic acid, wherein the ferulic acid or provides at least one UV-absorbing chromophore; and $b+f \geq 2$;

at least one of $X_3$ and $X_4$ is present; $X_3$ and $X_4$ are the same or different and are selected from the group consisting of a moiety characterized by the formula: —CH=CH—$(CH_2)_n CH_3$ where n ranges from 8 to 24; a moiety characterized by the formula: —NCO—$(CH_2)$—CH=CH—$(CH_2)_7 CH_3$; a sphingosine; a ceramide; and combinations thereof;

Y comprises an O, N, or S that is substituted or unsubstituted;

each a, b, c, e and f is $\geq 0$ and $a+b+c+e+f \geq 2$;

d is 0 or 1;

n1, n2, n3, n4, n5, and n6 represent the number of hydrogen atoms required to complete the undesignated valencies; and m ranges from 1 to 100 and each individual m unit is the same or different.

20. The composition of claim 19 wherein the compound having the $C_a$-$C_b$-$C_c$—$(Y)_d$—$C_e$-$C_f$ portion of formula I is a sphingosine or a ceramide.

21. A product comprising the composition of claim 19, wherein the product is a lotion, a sunscreen, a cosmetic product, an agrochemical, a pharmaceutical, a nutritional product or combinations thereof.

* * * * *